United States Patent [19]

Sengupta

[11] Patent Number: 4,562,176

[45] Date of Patent: Dec. 31, 1985

[54] METHOD AND COMPOSITION FOR TREATING CANCER

[76] Inventor: Sisir K. Sengupta, 978 Webster St., Needham, Mass. 02192

[21] Appl. No.: 538,240

[22] Filed: Oct. 3, 1985

[51] Int. Cl.⁴ .................... A61K 37/00; C07C 103/52
[52] U.S. Cl. .......................................... 514/17; 514/9; 260/112.5 R
[58] Field of Search ...................... 424/177; 514/17, 9; 260/112.5 R

[56] References Cited

PUBLICATIONS

Journal of Medicinal Chemistry, vol. 18, No. 12, 1975, pp. 1175–1180.
Journal of Medicinal Chemistry, 1979, vol. 22, No. 7, pp. 797–802.
Journal of Medicinal Chemistry, 1983, 26, 1631–1637.

*Primary Examiner*—Delbert R. Phillips

[57] ABSTRACT

Analogues of actinomycin D are provided which are effective in the therapeutic treatment of cancer. The analogues have a 1,4-oxazin-2-one or an oxazole ring or an extra quinone function.

4 Claims, No Drawings

METHOD AND COMPOSITION FOR TREATING CANCER

BACKGROUND OF THE INVENTION

This invention was made under Grant No. NCI-CA26281 from the National Institute of Health.

This invention relates to new analogues of actinomycin D and to a method of preparing them.

Actinomycin D (AMD) is disclosed in German Pat. No. 1,172,680 and is a chromopeptide antibiotic whose potent activity in several tumors, including Wilm's tumor, gestational choriocarcinoma and Kaposi's sarcoma, has been reported. It has the formula:

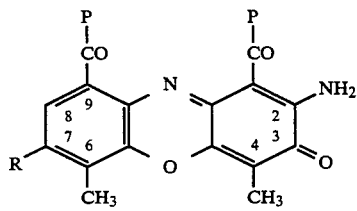

wherein P is

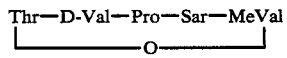

and R is hydrogen. AMD at submicromolar concentrations strongly inhibits DNA-dependent RNA synthesis and, to a lesser extent, DNA synthesis. Its interaction with DNA has been extensively studied, and the details of the mechanism is binding to DNA has been proposed, E. Reich, Cancer Res., 23, 1428 (1963), W. Muller and D. M. Crothers, J. Mol. Biol., 35, 251 (1968), and H. M. Sobell and S. C. Jain, J. Mol. Biol., 68, 21 (1972). It has been assumed that the cytotoxicity of AMD is due to its inhibition of RNA polymerase following the intercalative binding to DNA. It is quite possible, however, that the distortions in helical DNA resulting from the strong noncovalent association with AMD may not be solely responsible for the observed biological effects. For example, Nakazawa et al, J. Org. Chem., 46, 1943 (1981) suggest that an intermediate free-radical form of AMD may be the active form that causes DNA damage and cell death.

Furthermore, the proximal mechanism of biochemical action of AMD, which is evident from the inhibition of RNA synthesis, may not be the principal mechanism of selective cytotoxicity of the agent at the pharmacological level. For it is known that AMD is far more cytotoxic in those proliferating cells in which it inhibits DNA synthesis than in those of liver, kidney, muscle, etc., that are nonproliferating but are heavily dependent upon RNA synthesis for protein renewal.

Another pharmacological behavior of AMD is that it is not metabolized in vivo. Absence of metabolic conversion or detoxification of AMD leads to its accumulation in the cell nuclei of the host organs and causes cumulative toxicity. This acute cumulative toxicity limits the wide clinical application of AMD.

Accordingly, it would be desirable to synthesize new pharmacologically active analogues of AMD having increased drug efficacy. To achieve this, it would be desirable to increase the drug potency, by enhancing drug activity in the tumor cells and decrease toxicity to the host.

SUMMARY OF THE INVENTION

In describing this invention, the following notation as relates to the products of this invention is shown by Formula 2 and Formula 4.

Formula 2

| | R | $R_1$ | P |
|---|---|---|---|
| 2b | $C_6H_5$ | H | ppl |
| 2c | $C_6H_4Cl$ (o) | H | ppl |
| 2d | $C_6H_4Cl$ (m) | H | ppl |
| 2e | $C_6H_4Cl$ (p) | H | ppl |
| 2f | $C_6H_3Cl_2(2,4)$ | H | ppl |
| 2g | $C_6F_5$(pentafluorophenyl) | H | ppl |

Formula 4

| | R | P |
|---|---|---|
| 4a | $CH_3$ | ppl |
| 4b | $C_6H_5$ | ppl |
| 4c | $C_6F_5$ | ppl | wherein

P = 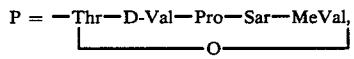

ppl (pentapeptidolactone)
P=—$N(C_2H_5)_2$, dea (diethylamine).

The compounds 2c through 2g and 4a through 4c are novel compounds. Compound 2b is not a novel compound and has been found to be active against mouse leukemia cells but has not been found active against human cancer cells. Compounds 2b through 2g and 4a through 4c are now found to be active and toxic against human cancer cells.

DESCRIPTION OF SPECIFIC EMBODIMENTS

A systematic study of structure-antitumor activity relationship on the chromophore substituted actinomycin D analogues was done. A variety and a series of AMD analogues 2-amino and 3-oxo substitutions into either a 1,4-oxazin-2-one or an oxazole ring were synthesized. In addition, a third analogue was prepared having an extra quinone function at the C-8 of the oxazole analogue. The biological and antitumor activities of the compounds were determined.

In all the analogous tested in accordance with this invention, the chemical integrity of the peptide lactones of the parent antibiotic is kept intact but their sterochemistry is altered. The analogoues are designed as transport modified prodrug forms of either the tricyclic active analogues of actinomycin D or actinomycin D itself. All analogues exhibit cytotoxicity that is several fold less potent than AMD; they also have no binding affinity towards extracellular DNA. Nonetheless, the analogues comprising this invention show improved antitumor activities (P388 leukemia, CDF$_1$ mice). Two of these analogues having a phenyl substituent at C-3 site of oxazinone ring (compound 2b) or C-2 position of 8-oxo-8H-oxazole ring (compound 4b) exhibit the highest human antitumor effects. Most of the analogues are active over a broader dose range than actinomycin D and are six to sixteen fold less cyctotoxic to human lymphoblastic leukemia (CCFR-CEM) cells in vitro. The analogues with the most pronounced antitumor activity are those which retain most elements in the peptide sterochemistry of actinomycin D, and have a quinone function or demonstrate susceptibility of their chromophores to biotransformation.

The compound of this invention having the formula:

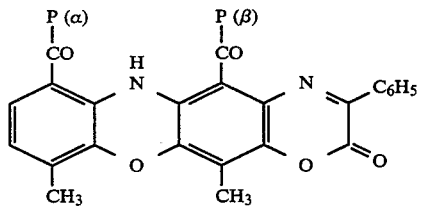

Compound 2b wherein P is pentapeptidolactone, is not novel and has been shown to be toxic against mouse leukemia cells. However, prior to this invention, this compound has not been shown to be toxic against human cancer cells. The compounds tested in accordance with this invention are set forth below as Formulas 1, 2, 3 and 4.

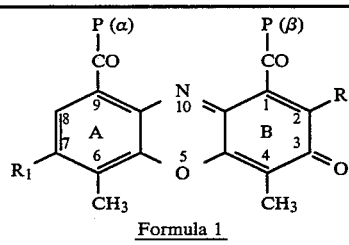

Formula 1

|    | R | R$_1$ | P |
|----|---|-------|---|
| 1a | AMD | NH$_2$ | H | ppl |
| 1b | 7-OH AMD | NH$_2$ | OH | ppl |
| 1c | 7-OMe AMD | NH$_2$ | OCH$_3$ | ppl |
| 1d |  | NH—CH—C$_6$H$_5$<br>       \|<br>      COOCH$_3$ | H | ppl |
| 1e |  | H | H | ppl |
| 1f |  | NH$_2$ | H | dea |
| 1g |  | NH$_2$ | OH | dea |
| 1h |  | NH—CH—C$_6$H$_5$<br>       \|<br>      COOCH$_3$ | H | dea |

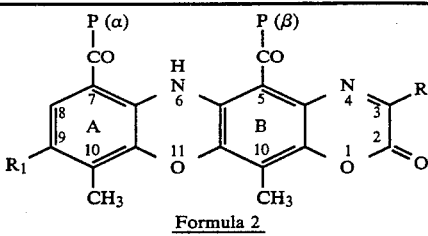

Formula 2

|    | R | R$_1$ | P |
|----|---|-------|---|
| 2a | CH$_3$ | H | ppl |
| 2b | C$_6$H$_5$ | H | ppl |
| 2c | C$_6$H$_4$Cl (o) | H | ppl |
| 2d | C$_6$H$_4$Cl (m) | H | ppl |
| 2e | C$_6$H$_4$Cl (p) | H | ppl |
| 2f | C$_6$H$_3$Cl$_2$ (2,4) | H | ppl |
| 2g | C$_6$F$_5$ (pentaflurophenyl) | H | ppl |
| 2h | C$_6$H$_{13}$ (n-hexyl) | H | ppl |
| 2i | C$_{10}$H$_7$ (2-naphthyl) | H | ppl |
| 2j | C$_6$H$_5$ | OCH$_3$ | ppl |
| 2k | CH$_3$ | H | dea |
| 2l | C$_6$H$_5$ | H | dea |

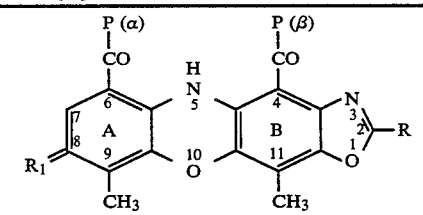

Formula 3

|    | R | R$_1$ | P |
|----|---|-------|---|
| 3a | CH$_3$ | H | ppl |
| 3b | C$_6$H$_5$ | H | ppl |
| 3c | C$_6$F$_5$ | H | ppl |
| 3d | C$_6$H$_5$ | OCH$_3$ | ppl |
| 3e | CH$_3$ | H | dea |
| 3f | C$_6$H$_5$ | H | dea |

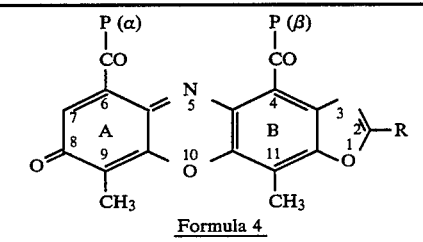

Formula 4

|    | R | P |
|----|---|---|
| 4a | CH | ppl |
| 4b | C$_6$H$_5$ | ppl |
| 4c | C$_6$F$_5$ | ppl |
| 4d | CH$_3$ | dea |
| 4e | C$_6$H$_5$ | dea | wherein

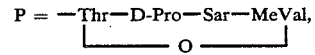

ppl (pentapepticolactone)
P=—N(C$_2$H$_5$)$_2$, dea (diethylamine).

The actinomycin D 1,4-oxazin-2-one analogues (compound 2) are obtained by reacting AMD with hydrogen in the presence of a hydrogenation catalyst such as platinum or palladium in a first step. The hydrogenated product then is reacted with a suitable alpha keto acid in an inert atmosphere such as nitrogen to produce one of the compounds 2a through 2l (AMD-OZN compounds).

The actinomycin D-5H oxazole analogues (compound 3) are obtained by reacting AMD with choral hydroate or hexafluoro acetone seaquihydrate in order to change the optical rotation of AMD from a negative to a positive value. The resultant product is reacted with an aldehyde to produce the compounds 3a to 3f wherein the R substituent is controlled by the choice of aldehyde.

The actinomycin D 8-oxo-8H-oxazale (AMD-OZL) analogues (compound 4) are prepared by reacting the corresponding compound 3a through 3f with 2,3-dichloro-5,6-dicyano-1,4-benzoquinone (DDQ) and refluxed in an inert atmosphere.

The new AMD-OZN analogues synthesized are 2c-2J and their physicochemical properties are given in Table 2 and 6. To examine the steric, lipophilic and electronegative effects of the substituents at C-3 position of AMD-OZN, the nature of the R groups in 2 is varied. Use of the appropriate α-keto (C, Scheme 1) produce the desired substituent R at C-3 of 2 and also at C-2 of 3 and 4 (Scheme 2 and 3). In Scheme 1, the steps followed for the preparation of the α-keto acids (C) and in Table 2, the properties of these acids described. Starting with the appropriate acid chlorides A,

TABLE 1

PROPERTIES OF α-KETO ACIDS (R—CO—COOH, SCHEME 1, C)

| | mp (°C.) | % Yield | Analyses |
|---|---|---|---|
| $C_6H_4Cl$ (o) | 76–78 | 66.5 | C,H,Cl |
| $C_6H_4Cl$ (m) | 61–63 | 64.5 | C,H,Cl |
| $C_6H_4Cl$ (p) | 67–69 | 60.2 | C,H,Cl |
| $C_6H_3Cl_2(2,4)$ | 80–83 | 58.4 | C,H,Cl |
| $C_6F_5$ (pentafluorophenyl) | 101–105 | 15.0 | C,H,F |
| $C_6H_{13}$ (n-hexyl) | 50–55 (dec) | 60.0 | C,H |
| $C_{10}H_7$ (2-naphthyl) | 80–85 | 61.8 | C,H[a] |

[a]Calcd: C,72.00; H,4.03. Found: C,71.39; H,3.71.

TABLE 2

PHYSICOCHEMICAL PROPERTIES OF ACTINOMYCIN D OXAZINONE (AMD-OZN) ANALOGUES (2)

| Compd | $R_f$[a] | % Yield | $[\alpha]_{644}^{20}$[b] | UV $\lambda_{max}$,nm ($\epsilon$)[c] | Mol Formula |
|---|---|---|---|---|---|
| 2c | 0.62 | 55 | −96.0 ± 12° (c 0.16) | 350 (10 200), 523 (5 750) | $C_{70}H_{89}N_{12}O_{17}Cl \cdot H_2O$ |
| 2d | 0.61 | 72 | −96.0 ± 16° (c 0.22) | 350 (9 800), 524 (5 510) | $C_{70}H_{89}N_{12}O_{17}Cl \cdot H_2O$ |
| 2e | 0.62 | 76 | −92.8 ± 18° (c 0.15) | 351 (11 100), 523 (6 290) | $C_{70}H_{89}N_{12}O_{17}Cl \cdot 2H_2O$ |
| 2f | 0.67 | 82 | −96.6 ± 16° (c 0.18) | 350 (8 500), 521 (4 830) | $C_{70}H_{88}N_{12}O_{17}Cl_2 \cdot H_2O$[d] |
| 2g | 0.29 | 11 | −88.0 ± 12° (c 0.11) | 350 (8 100), 526 (4 200) | $C_{70}H_{85}N_{12}O_{17}F_5$ |
| 2h | 0.43 | 32 | −100 ± 16° (c 0.20) | 320 (8 100), 401 (5 800) | $C_{70}H_{98}N_{12}O_{17}$[e] |
| 2i | 0.42 | 22 | −96.0 ± 12° (c 0.15) | 320 (8 100), 369 (6 200), 498 (6 100) | $C_{74}H_{92}N_{12}O_{17}$ |
| 2j | 0.31 | 11 | −86.0 ± 10° (c 0.11) | 350 (12 100), 526 (6 800) | $C_{71}H_{92}N_{12}O_{18} \cdot H_2O$ |
| Actinomycin (1a) | 0.55 | — | −300 ± 20° (c 0.10) | 424 (21 000), 442 (23 000) | $C_{62}H_{86}N_{12}O_{15} \cdot 2H_2O$ |

[a]$R_f$ in solvent, EtOAc—acetone, 2:1 (silica gel plates).
[b]In $CHCl_3$, concentration c in g/100 mL.
[c]In $CHCl_3$ solution (0.1–0.2 mM). Extinction values are concentration dependent.
[d]Calcd: C, 57.66; H, 6.04; N, 11.53; Cl, 4.87. Found: C, 57.46; H, 6.11; N, 11.27; Cl, 4.34.
[e]Calcd: C, 60.96; H, 7.11; N, 12.19. Found: C, 61.33; H, 7.01; N, 11.73.

TABLE 6

HPLC RETENTION TIMES AND ANTITUMOR ACTIVITY OF TETRACYCLIC CHROMOPHORIC ANALOGUES OF ACTINOMYCIN D, 2, 3 AND 4

| | $\frac{t_R}{min}$ (HPLC)[a] | In Vitro (CCRF-CEM)[b] $ID_{50}$, ng/mL | In Vivo P388 Assay Optimum Dose, μg/kg | MST,[c] days | % ILS[d] | Cure[e] |
|---|---|---|---|---|---|---|
| | | | control (no drug) | 11.0 | | 0/20 |
| 1a (Actinomycin) | 6.4 | 40 | 125 | 26 | 136 | 1/7 |
| 2b | 8.9 | 440 | 600 | 45 | 309 | 2/7 |
| 2c | 10.7 | 1800 | 1200 | 30 | 172 | 1/7 |
| 2d | 11.9 | 1600 | 600 | 29 | 164 | 0/7 |
| 2e | 11.0 | 1600 | 600 | 29 | 164 | 0/7 |
| 2f | 13.8 | 3200 | 1200 | 28 | 155 | 0/7 |
| 2g | 15.8 | 640 | 1800 | 31.5 | 186 | 1/7 |
| 2h | 16.7 | 2080 | 1200 | 25 | 127 | 0/7 |
| 2i | 7.7 | 1000 | 1200 | 26 | 136 | 0/7 |
| 3a | 17.0 | 2900 | 1200 | 21 | 91 | 0/7 |
| 3b | 19.7 | 9000 | 900 | 23 | 109 | 0/7 |
| 3c | 22.7 | 12500 | 1800 | 19 | 72 | 0/7 |
| 4a | 5.3 | 230 | 450 | 31 | 182 | 1/7 |
| 4b | 7.6 | 310 | 750 | 44 | 300 | 2/7 |

TABLE 6-continued
HPLC RETENTION TIMES AND ANTITUMOR ACTIVITY OF
TETRACYCLIC CHROMOPHORIC ANALOGUES OF ACTINOMYCIN D, 2, 3 AND 4

| | $\frac{t_R}{min}$ (HPLC)[a] | In Vitro (CCRF-CEM)[b] ID$_{50}$, ng/mL | In Vivo P388 Assay | | | |
|---|---|---|---|---|---|---|
| | | | Optimum Dose, μg/kg | MST,[c] days | % ILS[d] | Cure[e] |
| 4c | 11.2 | 630 | 900 | 30 | 172 | 1/7 |

[a]HPLC system: Varian Model #5020; C$_{18}$ column; solvent CH$_3$CN—5 mM NH$_4$OAc, pH 6.4, 62; 38; 1.5 mL/min.
[b]Human lymphoblastic luekemia cells in log-phase growth and in a suspension culture. Compounds were dissolved in Me$_2$SO medium, final growth medium contained 5% Me$_2$SO.
[c]10$^6$ P388 cells implanted intraperitoneally on day 0 into a group of 7 CDF$_1$ male mice. Drugs were administered, also ip, in 10% Me$_2$SO—saline on days 1,5,9. Test solutions were kept at 0–4° C., protected from light.
[c]MST = median survival time.
[d]% ILS = percent increase in life span.
[e]Over 60 day survivors. Average of 2 experiments. (Homogeniety of each test solution needs to be ascertained carefully by HPLC before the agents are tested).

SCHEME 1

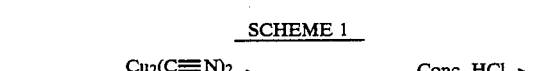

R—CO—COOH
C

Scheme 2

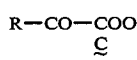

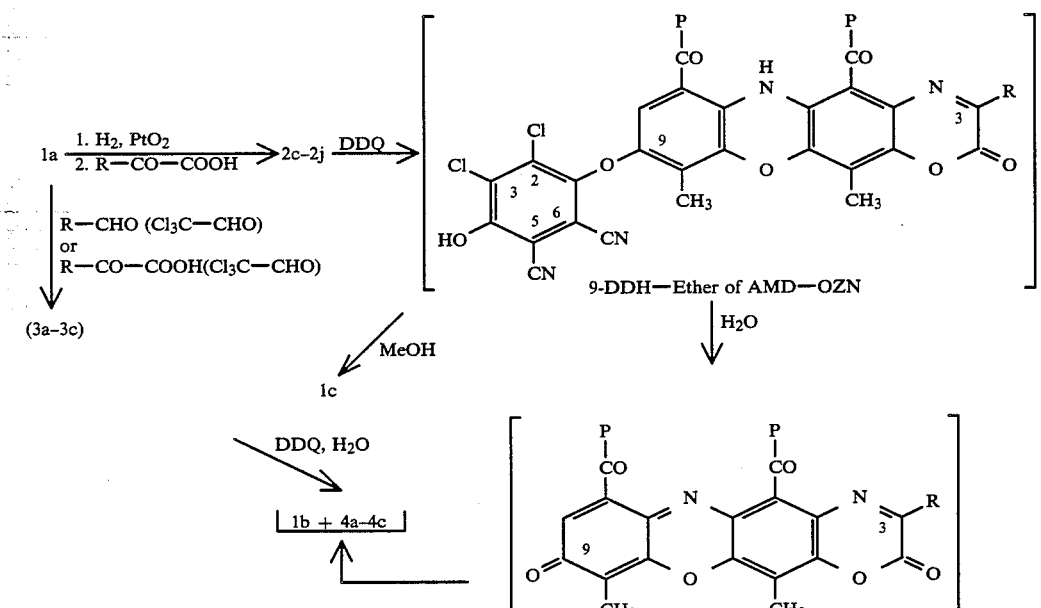

P = —Thr—D-Val—Pro—Sar—MeVal
          └————O————┘

SCHEME 3

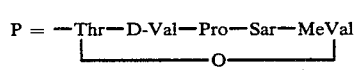

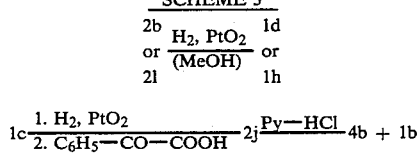

-continued
SCHEME 3

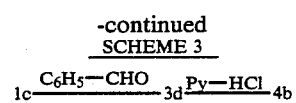

The 3e and 3f analogues are made by fusion of α-keto acids with 1f; in these reactions the α-keto acids acted as precursors of aldehydes. Alternatively, condensation reaction with aldehydes produced identical analogues via a concerted intramolecular hydrogen shift to the N-5 atom in 3a and 3f; this avoids the stepwise reduction of 1f to aminophenol prior to aldehyde condensation. However, with AMD. the condensation with "aldehydes" succeeds only with a treatment of actinomycin D by chloral prior to the condensation reactions. In this case, the procedure developed for the synthesis of 3e and 3f can not be applied directly for the synthesis of the AMD analogues 3a–3d, the properties of which are set forth in Table 3. Chloral hydrate is known to disengage the hydrogen bonding between 2-NH$_2$ and P$_\beta$ groups in AMD.

The physicochemical properties of the analogues 3a–3d (Table 3) are consistent with the expected structure. NMR data of the typical analogue 3b are shown in Table 5.

TABLE 3
PHYSICOCHEMICAL PROPERTIES OF OXAZOLO ANALOGUES OF ACTINOMYCIN D (3)

| compd | % Yield | R$_f$ | UV $\lambda_{max},\ nm\ (\epsilon)$a | $[\alpha]_D^{25}$ (c, CHCl$_3$)$^b$ | mol formula |
|---|---|---|---|---|---|
| 3a | 45 | 0.61 | 351 (7 900) 389 (11 300) | −101 ± 20° (c, 0.10) | C$_{68}$H$_{88}$N$_{12}$O$_{16}$·2H$_2$O$^c$ |
| 3b | 31 | 0.66 | 387 (10 900) | −110 ± 20° (c, 0.31) | C$_{69}$H$_{90}$N$_{12}$O$_{16}$·H$_2$O |
| 3c | 15 | 0.70 | 379 (8 100) | −90 ± 20° (0.15) | C$_{69}$H$_{85}$N$_{12}$O$_{16}$F$_5$ |
| 3d | 12 | 0.63 | 394 (12 100) | −110 ± 20° (c, 0.11) | C$_{70}$H$_{92}$N$_{12}$O$_{17}$·H$_2$O |

$^a$Using 50–100 μM solution in CHCl$_3$.
$^b$In a chloroform solution, concentration (c) in g/ml.
$^c$Calcd: C, 58.36; H, 6.69; N, 12.77. Found: C, 58.75; H, 6.39; N, 11.97.
R$_f$, TLC on silica gel plates using solvent, EtOAc—acetone, 2:1.

TABLE 5
COMPARISON OF NMR CHEMICAL SHIFTS$^a$ OF PROTONS IN 2-PHENYLOXAZOLE (3b) AND 2-PHENYL-8H—8-OXOOXAZOLE (4b) ANALOGUES OF ACTINOMYCIN D WITH CHEMICAL SHIFTS OF ACTINOMYCIN D

| Proton | δ | Proton (3b) | δ | Proton (4b) | δ |
|---|---|---|---|---|---|
| H$_7$$^b$ | 7.37 | H$_8$ | 6.91 | — | — |
| H$_8$$^b$ | 7.64 | H$_7$ | 7.06 | H$_7$ | 6.75 |
| 6-CH$_3$$^b$ | 2.56 | 9-CH$_3$ | 2.31 | 9-CH$_3$ | 2.67 |
| 4-CH$_3$ | 2.34 | 11-CH$_3$ | 2.28 | 11-CH$_3$ | 2.27 |
| D-Val NH (α or β) | 8.09, 7.94 | | 9.11, 8.82 | | 8.55, 8.48 |
| L-Thr NH (α or β) | 7.82, 7.20 | | 8.47, 8.30 | | 6.82, 6.73 |

$^a$CDCl$_3$ solution, 90-MHz spectrum, internal standard: tetramethyl silane.
$^b$H$_7$, H$_8$, 6-CH$_3$ and 4/CH$_3$ in AMD (1a) = H$_8$, H$_7$, 11-CH$_3$, and 9-CH$_3$ respectively in 3b and 4b.

The 4d and 4e analogues are made from 3e and 3f using 2,3-dichloro-5,6-dicyano-1,4-benzoquinone (DDQ) as the site specific oxidative agent. When the above oxidative reactions were applied on 3a–3c, the corresponding 8-oxo-8H-oxazolo [4,5-b] phenoxazine AMD analogues (4a–4c) are formed. These analogues also can be prepared from the AMD-OZN analogues 2a, 2b and 2g by the application of the same DDQ oxidation (Scheme 2).

Formation of both oxazinone (2) and oxazole (3) analogues increases the electrophilicity of the original aromatic ring A in 1; consequently, the ring A (in 2 and 3) becomes prone to electrophilic substitution by DDQ. The primary product of substitution of DDQ at C-9 of a typical analogue 2b is believed to be an intermediate hydroquinone ether (9-DDH-ether of 2b, Scheme 2). A reaction with protic agents, e.g., MeOH or H$_2$O displaces this ether substituent as 2,3-dichloro-5,6-dicyano-1,4-dihydroxybenzene (DDH). Thus, MeOH gives a 9-methoxy substituted analogue 2J which with a final loss of the protective 1,4-oxazinone ring is converted to 7-methoxy AMD (1c). A similar treatment of water on the intermediate 9-DDH-ether analogue gives an transient analogue (most probably with a hydroxy substituent at C-9 of 2b) which is promptly oxidized in air to 9-oxooxazinone intermediate compound. In the actinomycin D derived analogues, this intermediate derivative is found to be unstable and is converted to a mixture of AMD-OZL analogue and 7-hydroxy AMD (1b). However, a corresponding 9-oxooxazinone analogue with R=CH$_3$, derived from the same DDQ oxidation of the model analogue 2k is rather stable, and therefore, it can be isolated as a crystalline orange red solid.

The oxidation of the oxazole analogues, 3a–3c to 4a–4c follow the similar sequence of reactions; in this case, the tetracyclic analogues are quite stable and do not rearrange to 7-hydroxy or 7-alkoxy analogues. Thus, a DDQ reaction on 3b followed by a silica-gel and water treatment gives only 4b; a methanol treatment produces 3d. The compound 3d is prepared by condensing 1c with refluxing "benzaldehyde" in an oxygen-free atmosphere, which upon demethylation with the aid of pyridine hydrochloride in refluxing CHCl$_3$ solution (60°–80°) generated the above 4b (Scheme 3).

As a rule, the protective oxazole ring in structures 3 and 4 is more stable than the corresponding oxazinone ring in 2. For example, the pyridine-HCl demethylation of 2j is followed by rearrangement of the oxazinone ring resulting in a mixture of 4b and 1b. The same mixture of compounds, i.e., 4b and 1b is isolated when 2b is treated with DDQ and H$_2$O as mentioned above. Oxazinone ring in the intermediate 9-oxooxazinone undergoes transformation via either a contraction to an oxazole ring of 4b or a rearrangement to the tricyclic chrophoric analogue, 7-hydroxy AMD (1b).

The synthesis of the 7-hydroxy derivative of AMD (1b) from e.g., 2a is always accompanied with the formation on some 4a. Using $^{14}$C- and $^3$H-labeled 2a where $^{14}$Cr is evenly distributed among the C-2, C-3 and 3-methyl groups and $^3$H is restricted to the methyl groups, in the pentapeptidolactone moieties and also to the 10-and 12-methyl groups in the rings A and B only the conversion to 4a resulted in the loss of one third of the $^{14}$C label and 7-hydroxy AMD was free of any $^{14}$C label.

The compounds of the structure 2, suffer a rupture of the protective oxazinone during catalytic hydrogenation; in contrast, the analogues of 3 and 4 series are stable. For example, when 2b or 21 are hydrogenated in the presence of platinum, 1d and 1h are formed respectively. (Scheme 3).

As a rule, the AMD-OZL analogues (4a–4b) (Table 4) are more soluble in water than corresponding (2a–2b) and (3a–3b) analogues. The aqueous solubility of AMD is closely related to the unique conformation of the pentapeptide lactone rings P (both α and β) in 1a. Like actinomycin D, the compounds 4a and 4b are more soluble in water at 4° C. than at 20° C. and stick to glass surfaces. In actinomycin D, the peptide lactones (P, α and β) are interannularly hydrogen bonded primarily between the two D-Val residues; $P_B$ is further hydrogen bonded to a chromophoric 2-amino hydrogen through the β-threonine residues. This unique conformation is due to the planar tricyclic chromophore of AMD. Most of this characteristic is preserved in the tetracyclic AMD analogues 4a–4c. This conformation of AMD contributes to its molar ellipticity in CD spectra and the G-C base-pair specific binding properties (Table 7).

of the chromophoric 2-$NH_2$ group which influences the orientation of the β-threonine is responsible for this shift.

These along with the tetracyclic chromophore in analogures 2, 3 and 4 culminate in an observed loss of DNA binding properties (Table 7) studied either by the difference spectral or by the thermal denaturation of DNA ($\Delta T_m$) techniques.

In this respect all these tetracyclic analogues including 4a–4c differ from both AMD and 2-deamino-AMD. They don't seem to bind to DNA whereas AMD and

TABLE 4

PHYSICOCHEMICAL PROPERTIES OF 8-OXO-8H—OXAZOLO ANALOGUES (AMD-OZL) OF ACTINOMYCIN D (4)

| Compd | % Yield | $R_f{}^a$ | $[\alpha]_D$ (c, $CHCl_3$)[b] | $\lambda_{max}$, nm ($\epsilon$)c | Mol Formula |
|---|---|---|---|---|---|
| 4a | 28 | 0.36 | −242 ± 20° (c, 0.11) | 383 (17 300), 510 (11 700) | $C_{64}H_{86}N_{12}O_{17} \cdot 2H_2O$ |
| 4b | 55 | 0.41 | −220 ± 20° (c, 0.18) | 387 (19 900), 498 (13 700) | $C_{69}H_{88}N_{12}O_{17} \cdot 2H_2O$ |
| 4c | 19 | 0.48 | −201 ± 20° (c, 0.18) | 380 (17 900), 409 (12 300) | $C_{69}H_{83}N_{12}O_{17}F_5$ |

[a]$R_f$ on silica gel plates, EtOAc—acetone (2:1).
[b]c, concentration in g/ml.
[c]In $CHCl_3$ solution (≈80 μM).

TABLE 7

COMPARISON OF DNA BINDING PROPERTIES OF ACTINOMYCIN D, 7-HYDROXY ACTINOMYCIN D (1b) AND THE TETRACYCLIC CHROMOPHORIC ANALOGUES OF ACTINOMYCIN D, 3 AND 4

| Compd | $\Delta T_m$,[a] °C. | Diff. Absorption Spectra[b] −$\Delta\epsilon_{max}$(nm) | Diff. CD Spectra[c] −$\Delta[\theta]_{max}$(nm) |
|---|---|---|---|
| Actinomycin D (1a) | 7.1 ± 0.15 | 8,240(425) | 40,000(390) |
| 7-Hydroxy AMD (1b) | 6.7 ± 0.15 | 9,380(550) | 31,000(485) |
| 3a | 0.0 ± 0.30 | nil | nil |
| 4a | 1.0 ± 0.30 | nil | nil |

[a]$\Delta T_m = T_m$ of DNA-drug complex minut $T_m$ of purified calf-thymus DNA.
[b]Diff. Absorption Spectra is the calculated absorption spectra obtained by subtracting the spectrum of the DNA-bound analogue from the spectrum of the free analogue, measured at 340–600 nm.
[c]Diff. CD Spectra is the calculated CD Spectra obtained as the difference of the DNA-bound from the combined individual spectra of analogues and DNA at 340–600 nm.
Medium: 0.01 M phosphate containing $10^{-4}$ EDTA, buffer pH 7.0.

Therefore, as the planarity of the chromophore in 3a–3d is lost (in the same manner as in 2a–2j), the $[\alpha]_D$ values and [θ] values at 350–370 nm in these analogues are greatly reduced (Tables 2 and 3). The chromophore of the compounds in the 4 series appears planar, but it is tetracyclic rather than tricyclic. This chromophore in 4 also lacks the important 2-amino function present in AMD. The $[\alpha]_D$ and $[\theta]_{350-370}$ values in 4a are intermediate between the high value in AMD and the relatively low values in either 2a or 3a (Tables 2–4), which indicates a minimal change in the peptide conformation.

NMR data in Table 5 supports these conclusions. The chemical shifts of the protons in 3b (or 2b,2a) suggest a shielding effect on the aromatic ring protons $H_8$ and $H_7$ in 3b due to an increase in the electron density in ring A. The C-11 and C-9 methyls in 3b exhibit closer chemical shifts compared to AMD because both A and B rings are aromatic. The chemical shifts of D-val NH and β-threonine NH protons relate to the conformation of the chromophore and peptide lactones. The data in Table 5 show that the δ-values of these protons in 3b are shifted farthest from those in AMD. In 4b, the δ-values for D-val NH are about the same as in AMD; this is not true for the chemical shifts of L-threonine NH. The lack 2-deamino AMD binds to DNA strongly by intercalation (Table 7).

The tumor-inhibitory activities of these tetracyclic analogues may depend on the biotransformation of the tetracyclic chromophores. The chromophores of AMD-OZN (2) and AMD-OZL (4) have been found to be biolabile. Further, 4 has a quinone function which may participate in tumor growth inhibition.

In vitro growth inhibition of the analogues were assayed against human lymphoblastic leukemia cells (CCRF-CEM) in log phase. Results are shown in Table 6. The most cyctoxic are AMD-OZN analogues 2b and 2g and AMD-OZL analogues 4a–4c. However, compared to AMD, they are several fold less cytotoxic to CEM-cells in vitro. These results could be due to the altered uptake and retention of the agents by the specific cells, or to rates of extracellular and/or intercellular activation or deactivation.

These analogues were tested for antitumor activity against P388 lymphocytic leukemia in male $CDF_1$ hybrid mice (Table 6). The tumor was implanted intraperitoneally (ip) with $10^6$ cells. The drugs were administered once daily on days 1, 5, 9 beginning 1 day after implantation. Compounds were tested over a range of doses, but only the optimal nontoxic doses are listed. In this system, analogues of the series 2 and 4 (Table 6) in general showed improved biological activity. Of these, the two most active agents are 2b and 4b. They show superior activity (%ILS) and ability to produce long-term survivors. The same 2b analogue exhibited similar high activity against P388 in $BDF_1$ mice at qd 1–4 schedule.

The effect of halogen substitution was investigated on the 2-phenyl ring or the substituents like long-chain alkyl or larger aromatic naphthyl ring at the C-2 site of w. The lipophilicity of the agent was increased in general ($t_R$ values, HPLC) without enhancing the effectiveness as measured by %ILS. However, all of these analogues 2b–2g (except 2h and 2j) and 4a–4c analogous showed high levels of activity over much broader dose ranges. This property differs distinctly from AMD which has a remarkably narrow dose reponse curve in man.

The compounds of this invention can be administered to an average 70 kg human patient at a dosage of between about 1 and about 15 mg, preferably between about 1 and 10 mg daily. The compounds can be administered orally or intravenously.

The following examples illustrate the present invention and are not intended to limit the same.

Melting points were determined on a Thomas-Hoover melting point apparatus at a heating rate of 2° C./min. Dry column chromatography was accomplished with silicic acid powder (Bio-Sil A 100–200 mesh, Bio-Rad Laboratories, Inc.) or acid alumina (Woelm grade 1). Thin layer chromatography was performed on silica gel plates (Brinkmann Instrument, Inc.). For oxazinone analogues (2b), the silica gel plates were exposed to the vapor of conc. HCL in an air-tight container for 20 min before application of the compound for TLC. This procedure helped to prevent the streaking of the compounds in the chromatogram. Solvent systems were (A) EtOAc-acetone (2:1); (B) dry t-BuOH-$C_6H_6$—$C_6H_5N$ (85:12.5:2.5); (C) Cifferri, the organic phase of the mixture EtOAc-MeOH-$H_2O$ (20:L:20). High performance-liquid chromatography was carried out on a Varian Model 5020 gradient liquid chromatograph equipped with CD-111L chromatography data system and fitted with Varian reversed-phase $C_{18}$ column with isocratic solvent systems, $CH_3CN$-5 mM $NH_4OAc$ buffer, pH 6.4 (68:32), flow rate 15 mL/mn, with UV-visible variable and fixed wavelength dual detectors at 254, 440, 500 and 252 nm. Spectra were determined on the following instruments: IR spectra were obtained on the Perkin-Elmer Model 237 Infra Cord with KBr micropellets or in $CHCl_3$ solutions; UV-visible spectra were obtained on a Gilford 250 spectrophotometer, which, with the addition of a baseline reference compensator (Analog Multiplexer 5053) and thermoprogrammer, auto four cell programmer and thermoelectric cell holder 2577, were used to obtain thermal denaturation curves; specific rotational values were determined in $CHCl_3$ solutions using a Cary 60 spectropolarimeter; NMR spectra were obtained in a JOEL FQ −90 MHz spectrometer equipped with Fourier transform. All elemental analyses were within +0.4%, unless it is specified otherwise.

EXAMPLE I

SYNTHESIS OF 3-SUBSTITUTED ACTINOMYCIN D OXAZINONES. PROCEDURE FOR 3-(2-NAPHTHYL)-10,12-DIMETHYL-2H,6H-OXAZINO[3,2-b]PHENOXAZINE-2-ONE 5,7-BIS[CARBONYL-L-THREONYL-D-VALYL-L-PROLYLSARCOSYL-L-N-METHYLVALINE-(THREONINE HYDROXYL)] LACTONE, (2b).

GENERAL METHOD

AMD (1a; 75 mg 0.06 mmol) was reduced with $PtO_2$ and hydrogen in methanol (25 mL). The reddish yellow color of the reaction mixture was discharged and at this stage the reduced reaction mixture was filtered into a second flask filled with nitrogen and containing a solution of 2-naphthoyl formic acid C, R=$C_{10}H_7$, Scheme 1) in MeOH (25 mL). This reaction mixture was stirred for 5 h at ambient temperature always maintaining the nitrogen atmosphere; at the end of reaction, the volume was reduced to about 1 mL under vacuum and the concentrate was dissolved in ethyl acetate (50 mL) and washed with water (5×10 mL) until it was acid-free (pH above 5). The residue from the dried ($Na_2SO_4$) and evaporated ethyl acetate fraction was chromatographed on silicic acid with $CHCl_3$-acetone (2:1 and 1:1). The process yielded pure AMD-OZN compound 2i in 1:1 $CHCl_3$-acetone fraction. Yield 18 mg; $R_f$ (TLC), $t_R$ (HPLC), UV-absorption, specific rotation values and microchemical analysis (C, H, N) of this AMD-OZN are described in Tables 2 and 6.

EXAMPLE II

SYNTHESIS OF 2-PHENYL-9,11-DIMETHYL-5H-OXAZOLO[4,5-b]PHENOXAZINE 4,6-BIS[CARBONYL-L-THREONYL-D-VALYL-L-PROLYLSARCOSYL-L-N-METHYL-VALINE-(THREONINE HYDROXYL)] LACTONE, 3b.

GENERAL METHOD

A solution of AMD (50 mg, 0.04 mmol) in methanol-water (10:1, 50 mL) was allowed to react with chloral (0.5 mL, bp 97°–99°) at ambient temperature and during this period, the optical rotation changed from the negative to a positive value and became steady after the end of 30–32 h. The change in the cotton effect in AMD is a consequence of the disruption of the strong hydrogen bonding between 2-amino hydrogen and β-peptide lactone group. After this treatment, benzaldehyde (4 mL, bp 279°) was added and the mixture was heated under $N_2$ at 50°–55°/18 mm until all the chloral, water and methanol were removed. The residual mixture was then stirred under $N_2$ at 180° for 7 h till TLC or HPLC showed no trace of AMD. The reaction mixture was evaporated at 60°/4 mm to remove all unreacted benzaldehyde. The residue which contained some benzoic acid was triturated with $NaHCO_3$ and after TLC (solvent B, $R_f$ 0.51) solid 16.3 mg (31%) was obtained. Tables 2 and 6 give the physiocochemical characteristics and microchemical analytical data for this and the other oxazole analogues in the 3 series.

EXAMPLE III

SYNTHESIS OF 2-SUBSTITUTED ACTINOMYCIN D 8-OXO-8H-OXAZOLES (AMD-OZL) ANALOGUES. SYNTHESIS OF 2-PHENYL-9,11-DIMETHYL-8-OXO-8H-OXAZOLO[4,5-b]PHENOXAZINE 4,6-BIS[CARBONYL-L-THREONYL-D-VALYL-L-PROLYLSARCOSYL-L-N-METHYLVALINE-(THREONINE HYDROXYL)] LACTONE, (4b).

GENERAL PROCEDURE

A solution of 3b (140 mg 0.1 mmol) in p-dioxane (15 mL) and DDQ (150 mg) was refluxed for 3 h under $N_2$. DDQ was added in 3 equal portions of 50 mg, first at the beginning of the reaction and then at the end of the first and the second hours. At the end of reaction, the dioxane was evaporated under reduced pressure and the red brown solid was chromatographed on silica-gel TLC plates in solvent system B. The bands represented DDQ, $R_f$0.67; the reaction product, $R_f$0.3–0.35, which, in all probability, is a 8-DDH ether of 3 (R=$C_6H_5$, $R_1$=2,3-dichloro-5,6-dicyano-4-hydroxy-phenoxy).

The third fluorescent band at or near the origin $R_f$ 0.02–0.07 was identified as that of DDH (2,3-dichloro-5,6-dicyano-1,4-dihydroxy benzene). The middle band, after extraction with benzene and dioxane, gave flaky dark brown solid, 100 mg (65%). IR showed an additional band for —C≡N at 4.85μ. A portion of this intermediate phenoxy ether (60 mg) was stirred with dioxane-water (10 mL, 95:5) for 24 h. After evaporation, the residue was chromatographed on Woelm alumina and then on silicic acid eluting first with Cifferri and then with solvent A. The combined fractions in solvent A showed only one spot on TLC (solvent A), $R_f$ 0.41; yield 45 mg (55%) of purple solid. See Tables 4–6 for detailed properties of this and other AMD-OZL (4) analogues. Another portion (35 mg) of the compound from the above purple band, $R_f$ 0.3–0.35 was refluxed in dry methanol (5 mL) for 3 h. After chromatographic purification, a reddish-brown solid of another compound 3d, $R_f$ 0.63 (TLC, Solvent A) was obtained, yield 25 mg (50%). See Table 3 for the physicochemical data of this compound. The yields in Table 3 are based on either the fusion of α-keto acids or the condensation the aldehydes (Scheme 2).

EXAMPLE IV

CONVERSION OF 3d TO 4b

A mixture 20 mg of the above 3d analogue and pyridine hydrochloride (200 mg) in chloroform (20 mL) was refluxed for 18 h. The residue upon evaporation was dissolved in dichloromethane, washed successively with 1N HCl, 0.5M NaHCO$_3$ and dried over Na$_2$SO$_4$. After TLC (solvent A) and crystallization from methanol, purple solid (16 mg, 85%; $R_f$ 0.41, TLC solvent A), identical with 4b was recovered (Scheme 3).

EXAMPLE V

CATALYTIC REDUCTION OF 2b AND 21 TO 1d AND 1h RESPECTIVELY

A solution of the above tetracyclic analogue 2b (45 mg, 0.03 mmol) in methanol (35 mL) was hydrogenated in the presence of PtO$_2$. As the pale green colored reduction mixture was being filtered, the filtrate started turning deep yellow in contact with air showing the generation of the tricyclic phenoxazinone chromophore of AMD. Evaporation and purification of the residue on TLC (solvent A) gave a major band, ($R_f$ 0.76) of 1d, mp 218–220 (dec), $[\alpha]^{20}_D$ −295±20° (c,0.1 CHCl$_3$), UV $\lambda_{max}$ 420 nm, ($\epsilon$12 800); yield upon elution with MeOH, 40 mg (87%). All attempts to remove the 1-methoxycarbonylbenzyl substituent chain on $N^{2-}$ site of 1d by hydrogenolysis were unsuccessful, probably because of the presence of the methoxycarbonyl group. Anal. (C$_{71}$H$_{94}$N$_{12}$O$_{18}$.H$_2$O) C, H, N.

Compound 1H was generated as above from 21: mp 152° C.: UV $\lambda_{max}$ (CHCl$_3$) 424 nm ($\epsilon$ 14 800); $R_f$ 0.61 (TLC, solvent A) for 1 h. For 21: mp 163–167; UV $\lambda_{max}$ (CHCl$_3$) 502 nm ($\epsilon$ 111 200); $R_f$ 0.39 (solvent A), Anal. (C$_{33}$H$_{38}$N$_4$O$_6$ for 1 h), (C$_{32}$H$_{34}$N$_4$O$_5$ for 21) C, H, N.

EXAMPLE VI

CONVERSION OF 2b TO A MIXTURE OF 4b AND 1b VIA DDQ OXIDATION

Above 2b.2H$_2$O (135 mg, 0.1 mmol) and DDQ (70 l mg, 0.3 mmol) in 25 mL MeOH was refluxed for 1 h under N$_2$. The mixture was evaporated to dryness and the residue was dissolved in CH$_2$Cl$_2$ (50 mL) and filtered to remove the precipitated DDH and DDQ. The filtrate was passed through an acidic alumina column which freed it from the residual DDH and DDQ; the eluent in CH$_2$Cl$_2$ which contained the intermediate 9-oxooxazinone analogue (Scheme 2) and showed consistent streakings on TLC (solvents A, B, C), without further purification was treated with 10 g of silica powder in 50% EtOH (30 mL) for 2 h. The suspension, after filtration and concentration, was banded on TLC (solvent B). Bands of 4b, $R_f$ 0.59 and 1b, $R_f$ 0.21 (no traces of starting 2b) were extracted in MeOH and were subjected to HPLC on a reversed phase C$_{18}$ column (CH$_3$CN-5 mM NH$_4$O)Ac, pH 6.4, 68:32, 1.5 mL/min). Fractions corresponding to $t_R$ 2.7 (7-OH AMD, 1b, yield 36%), $t_R$ 5.6 min (4b, yield 33%) were collected. These fractions were purified once more by HPLC to obtain samples of high purity and homogeniety.

EXAMPLE VII

SOLUBILITY OF ACTINOMYCIN D AND ANALOGUES 2b, 3b AND 4b IN DISTILLED WATER AT 20° C. AND 4° C.

The solubility of the above analogues which were determined from their O.D values at their respective $\lambda_{max}$ nm are as follows: solubility of AMD, 0.9 mg/mL at 20° C. and 20.5 mg/mL at 4° C.; that of 4b, 1.7 mg/mL at 20° C. and 11 mg/mL at 4° C.; solubility of 3b at 20° C., 0.3 mg/mL and 4° C., 1.2 mg/mL; 2b, 0.6 mg/mL (20° C.), 2.2 mg/mL (4° C.).

EXAMPLE VIII

DNA-DRUG BINDING BY DIFFERENCE SPECTRAL AND THERMAL DEVATURATION OF DNA ($\Delta T_m$) TECHNIQUES These experiments were performed according to the methods described by Sengupta et al., *Cancer Chemother. Rep.*, 1974, 58, p. 35, Sengupta et al, *J. Med. Chem.*, 1981, 24, p. 1052 and Sengupta et al, 1983, 26, p. 448, Sengupta et al, 1978, *Biochem. Biophys Acta*, 521, p. 89.

I claim:

1. A composition of matter active as a toxic agent against cancer cells sensitive to actinomycin D, said composition having the formula:

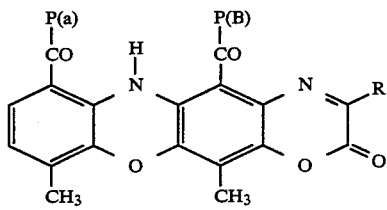

wherein R is selected from the group consisting of C$_6$H$_4$Cl (o), C$_6$H$_4$Cl (m), C$_6$H$_4$Cl (p), C$_6$H$_3$Cl$_2$ (2,4) and C$_6$F$_5$ (pentaflurophenyl), and P is pentapeptidolactone.

2. A composition of matter active as a toxic agent against cancer cells sensitive to actinomycin D, said composition having the formula:

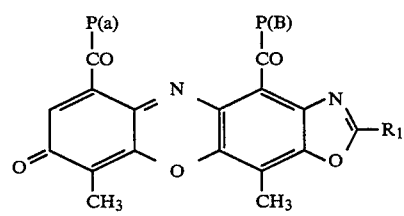

wherein R$_1$ is selected from the group consisting of CH$_3$, C$_6$H$_5$, C$_6$F$_5$ (pentafluorophenyl), and P is pentapeptidolactone.

3. A process of therapeutically treating a patient having cancer cells sensitive to actinomycin D comprising the steps of:

administering to the patient a compound selected from the group consisting of:

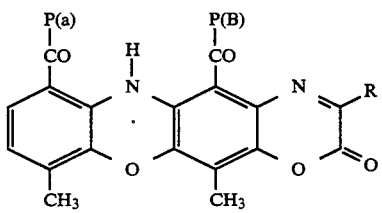

wherein R is selected from the group consisting of $C_6H_5$, $C_6H_4Cl$ (o), $C_6H_4Cl$ (m), $C_6H_4Cl$ (p), $C_6H_3Cl_2$ (2,4), $C_6F_5$ (pentaflurophenyl), and P is pentapeptidolactone.

4. The process of therapeutically treating a patient having cancer cells sensitive to actinomycin D comprising the step of:

administering to the patient a compound selected from the group consisting of:

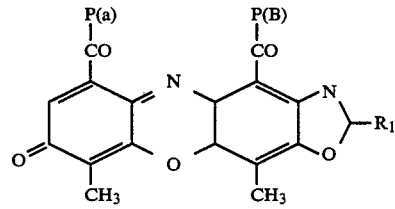

wherein $R_1$ is selected from the group consisting of $CH_3$, $C_6H_5$, $C_6H_5$, and P is pentapeptidolactone.

* * * * *